(12) United States Patent
Neuharth (10) Patent No.: US 12,059,173 B2
(45) Date of Patent: Aug. 13, 2024

(54) MAGNETICALLY DRIVEN ATHERECTOMY SYSTEM (71) Applicant: BOSTON SCIENTIFIC SCIMED, INC., Maple Grove, MN (US)

(72) Inventor: Jarrod Kenneth Neuharth, Brooklyn Center, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 96 days.

(21) Appl. No.: 17/510,911

(22) Filed: Oct. 26, 2021

(65) Prior Publication Data

US 2022/0125475 A1 Apr. 28, 2022

Related U.S. Application Data

(60) Provisional application No. 63/106,164, filed on Oct. 27, 2020.

(51) Int. Cl.
*A61B 17/3207* (2006.01)
*A61B 17/00* (2006.01)

(52) U.S. Cl.
CPC ......... *A61B 17/320758* (2013.01); *A61B 2017/00473* (2013.01); *A61B 2017/00477* (2013.01); *A61B 2017/00876* (2013.01)

(58) Field of Classification Search
CPC .. A61B 17/320758; A61B 2017/00473; A61B 2017/00477; A61B 2017/00876;
(Continued)

(56) References Cited

U.S. PATENT DOCUMENTS 5,431,673 A * 7/1995 Summers ....... A61B 17/320783
606/171
5,667,490 A * 9/1997 Keith ............. A61B 17/320758
604/905

(Continued)

FOREIGN PATENT DOCUMENTS

WO 2004080507 A1 8/2018

OTHER PUBLICATIONS

International Search Report and Written Opinion dated Jan. 26, 2022 for International Application No. PCT/US2021/056616.

*Primary Examiner* — Elizabeth Houston
*Assistant Examiner* — Lindsey Bachman
(74) *Attorney, Agent, or Firm* — Seager, Tufte & Wickhem, LLP (57) ABSTRACT

An atherectomy system includes a multiple use assembly and a single use assembly that is adapted to releasably engage with the multiple use assembly. The multiple use assembly includes a drive motor having an output shaft, a first magnetic coupling segment that is rotatably coupled to the output shaft and a circuit that is adapted to control operation of the drive motor. The single use assembly, intended to be disposable, includes a second magnetic coupling segment that is adapted to rotatably engage the first magnetic coupling segment, a spline shaft that is rotatably coupled with the second magnetic coupling segment, a drive gear assembly that is translatable along the spline shaft, and a drive shaft that is operably coupled with the drive gear assembly and is adapted to rotatably engage an atherectomy burr.

10 Claims, 4 Drawing Sheets

(58) Field of Classification Search
CPC ........ A61B 2017/0046; A61B 17/3207; A61B 17/320016
USPC .................................................... 606/159, 1
See application file for complete search history.

(56) References Cited

U.S. PATENT DOCUMENTS

| | | | |
|---|---|---|---|
| 5,899,915 A | 5/1999 | Saadat | |
| 2002/0161384 A1* | 10/2002 | Wulfman | A61B 17/320758 606/159 |
| 2007/0156125 A1* | 7/2007 | DeLonzor | A61B 18/0218 606/1 |
| 2010/0217245 A1* | 8/2010 | Prescott | A61B 17/1624 606/1 |
| 2011/0077673 A1* | 3/2011 | Grubac | A61B 17/3207 606/159 |
| 2013/0066304 A1* | 3/2013 | Belson | A61B 34/37 606/1 |
| 2013/0253552 A1* | 9/2013 | Schoenle | A61B 17/320758 606/159 |
| 2014/0148835 A1 | 5/2014 | Schmitz et al. | |
| 2017/0273698 A1* | 9/2017 | McGuckin, Jr. | A61B 17/320758 |
| 2018/0242998 A1 | 8/2018 | Dhandhusaria et al. | |
| 2019/0262032 A1* | 8/2019 | Carlson | G05B 11/42 |
| 2019/0262034 A1* | 8/2019 | Spangler | A61B 17/320758 |
| 2020/0060718 A1 | 2/2020 | Patel et al. | |
| 2020/0229844 A1 | 7/2020 | Rawson et al. | |
| 2020/0315654 A1* | 10/2020 | Patel | A61B 17/1204 |
| 2020/0360047 A1* | 11/2020 | Kelly | A61B 17/320758 |
| 2021/0145477 A1* | 5/2021 | Shaw | A61B 17/3403 |

\* cited by examiner

MAGNETICALLY DRIVEN ATHERECTOMY SYSTEM

CROSS REFERENCE TO RELATED APPLICATIONS

The present application claims the benefit of and priority to U.S. Prov. Pat. App. No. 63/106,164, filed Oct. 27, 2020 and titled MAGNETICALLY DRIVEN ATHERECTOMY SYSTEM, the disclosure of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, atherectomy system includes a multiple use assembly and a single use assembly that is releasably engageable with the multiple use assembly. The multiple use assembly includes a drive motor having an output shaft and a first magnet coupling segment that is rotatably coupled to the output shaft. The multiple use assembly includes a controller that is adapted to control operation of the drive motor. The single use assembly includes a second magnetic coupling segment that is adapted to rotatably engage the first magnetic coupling segment and a spline shaft that is rotatably coupled with the second magnetic coupling segment. A drive gear assembly is translatable along the spline shaft. A drive shaft is operably coupled with the drive gear assembly and is adapted to rotatably engage an atherectomy burr.

Alternatively or additionally, the multiple use assembly may further include a user interface that is operably coupled with the controller.

Alternatively or additionally, the multiple use assembly may include one or more printed circuit boards that include the controller.

Alternatively or additionally, the multiple use assembly may further include a multiple use assembly housing.

Alternatively or additionally, the drive motor may be disposed within the multiple use assembly housing.

Alternatively or additionally, the controller that is adapted to control operation of the drive motor may be disposed within the multiple use assembly housing.

Alternatively or additionally, the single use assembly may further include a gear housing that is adapted to translate relative to the spline shaft.

Alternatively or additionally, the atherectomy system may further include a pumping section disposed within the gear housing.

Alternatively or additionally, the atherectomy system may further include a pump rotor that is operably secured to the drive shaft and disposed within the pumping section.

Alternatively or additionally, the single use assembly may further include a translation handle coupled to the gear housing, such that translating the translation handle causes the gear housing to translate relative to the spline shaft.

In another example, an atherectomy system includes a housing. A drive motor is disposed within the housing and includes an output shaft that extends to an exterior of the housing. A controller is disposed within the housing and is adapted to control operation of the drive motor. A first magnetic coupling segment is rotatably coupled to the output shaft exterior to the housing. The atherectomy system includes a single use assembly. The single use assembly includes a second magnetic coupling segment that is adapted to rotatably engage the first magnetic coupling segment and a spline shaft that is rotatably coupled with the second magnetic coupling segment. A drive gear assembly is translatable along the spline shaft and is operably coupled with a drive shaft that is adapted to rotatably engage an atherectomy burr.

Alternatively or additionally, the single use assembly may further include a gear housing that is adapted to translate relative to the spline shaft.

Alternatively or additionally, the atherectomy system may further include a pumping section that is disposed within the gear housing.

Alternatively or additionally, the atherectomy system may further include a pump rotor that is operably secured to the drive shaft and is disposed within the pumping section.

Alternatively or additionally, the single use assembly may further include a translation handle coupled to the gear housing such that translating the translation handle causes the gear housing to translate relative to the spline shaft.

In another example, an atherectomy system includes a housing and a drive motor that is disposed within the housing. The drive motor includes an output shaft that extends to an exterior of the housing. A controller is disposed within the housing and is adapted to control operation of the drive motor. The atherectomy system includes a magnetic coupling segment that is rotatably coupled to the output shaft exterior to the housing and is adapted to releasably and rotatably engage a single use assembly in order to rotate an atherectomy burr forming part of the single use assembly, the drive motor adapted to rotate the atherectomy burr at rotational speeds exceeding 100,000 revolutions per minute.

Alternatively or additionally, the single use assembly includes a second magnetic coupling segment adapted to rotatably engage the first magnetic coupling segment, a spline shaft that is rotatably coupled with the second magnetic coupling segment, a drive gear assembly that is translatable along the spline shaft and a drive shaft that is operably coupled with the drive gear assembly and is adapted to rotatably engage the atherectomy burr.

Alternatively or additionally, the single use assembly may further include a gear housing that is adapted to translate relative to the spline shaft.

Alternatively or additionally, the single use assembly may further include a translation handle that is coupled to the gear housing, such that translating the translation handle causes the gear housing to translate relative to the spline shaft.

Alternatively or additionally, the single use assembly may further include a pump rotor that is operably secured to the drive shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material (e.g., blocked by an occlusion). In an atherectomy procedure, a device on an end of a drive shaft that is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction. In some cases, atherectomy involves using an abrasive atherectomy burr that is rotated at high speeds exceeding 100,000 revolutions per minute (RPM) in order to abrade plaque and other hardened materials from within the patient's vessel. Atherectomy burrs may be rotated at speeds exceeding 140,000 RPM, and even at speeds as high as 180,000 RPM.

Figure 1:
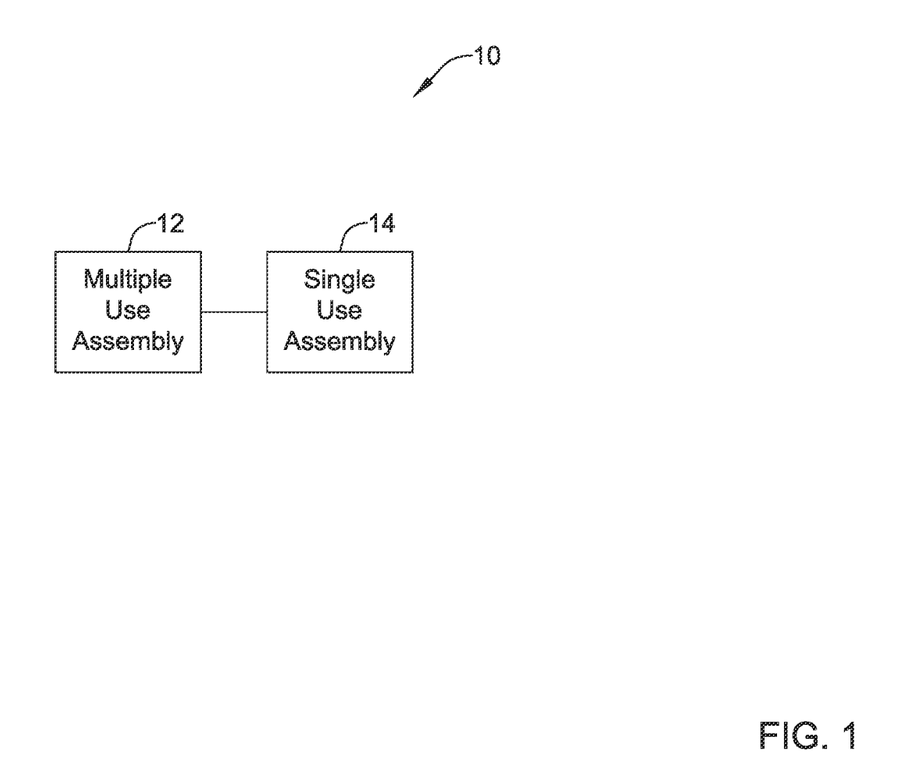
FIG. 1 is a schematic block diagram of an illustrative atherectomy system.

FIG. 1 is a schematic block diagram of an illustrative atherectomy system 10. In some cases, the atherectomy system 10 may be considered as including a multiple use assembly 12 and a single use assembly 14. As will be discussed, the multiple use assembly 12 may include some of the more expensive components such as a drive motor and the electronics necessary to control operation of the drive motor. The multiple use assembly 12 may include a user interface, for example. The multiple use assembly 12 may be considered as being intended to be used over and over again. Being able to use the multiple use assembly 12 a plurality of times can provide cost savings. Because the multiple use assembly 12 is sealed against contaminants, a plurality of single use assemblies 14 may be used with the multiple use assembly 12, one after the other.

As an example, a particular single use assembly 14 may include a drive shaft having a particular length, and an operator may discover in the middle of an atherectomy procedure that the drive shaft is either too short or too long. The operator may withdraw the drive shaft of that particular single use assembly 14 from the patient's vasculature and that particular single use assembly 14 may be thrown away, and a new single use assembly 14 having a drive shaft of more appropriate length may be coupled with the multiple use assembly 12 and the atherectomy procedure may continue. It will be appreciated that this is merely illustrative, as there are any variety of reasons to change to a different single use assembly 14 during an atherectomy procedure.

In some cases, for example, a first single use assembly 14 may be used for a first patient and then disposed of, and a second single use assembly 14 may be used for an atherectomy procedure performed on a second patient. One way to consider the illustrative atherectomy system 10 is that the multiple use assembly 12, may be considered as the "dry" part of the atherectomy system 10. Conversely, the single use assembly 14 may be considered as the "wet" part of the atherectomy system 10. The single use assembly 14 may, for example, include saline that is provided within a drive shaft. There is no fluid transfer between the "wet" part of the atherectomy system 10 and the "dry" part of the atherectomy system 10. Moreover, it will be appreciated that the "dry" part of the atherectomy system 10, may be re-sterilized and re-used with a subsequent patient. This can provide cost savings, as the components within the "dry" part don't have to be replaced with each atherectomy process.

The multiple use assembly 12 may be sterilized and subsequently re-sterilized after use, via any of a variety of different sterilization processes. For example, the multiple use assembly 12 may be exposed to an ethylene oxide atmosphere in order to sterilize the multiple use assembly 12. It will be appreciated that it is only necessary to sterilize the outer surfaces of the multiple use assembly 12. In some instances, the multiple use assembly 12 may be subjected to a radiative sterilization process such as e beam radiation or gamma radiation.

As will be discussed, the atherectomy system 10 may include a magnetic coupling between the multiple use assembly 12 and the single use assembly 14 such that the drive motor within the multiple use assembly 12 may easily and cleanly rotatably engage the drive shaft provided as part of the single use assembly 14. In some cases, use of a magnetic coupling permits contactless torque transmission from the drive motor to an atherectomy burr. Use of a magnetic coupling seals the drive motor against fluid ingress. Because the multiple use assembly 12 is sealed against fluid ingress, the multiple use assembly 12 remains cleaner and is easily re-sterilized before subsequent re-use.

Figure 2:
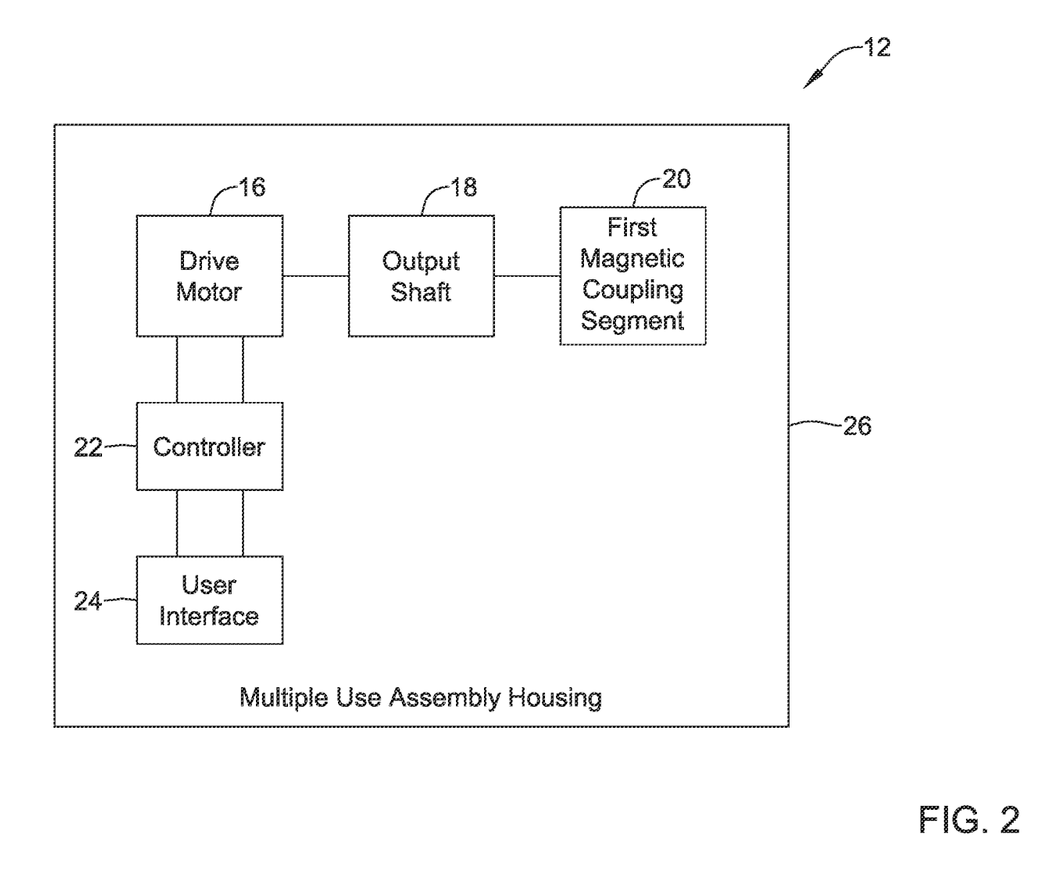
FIG. 2 is a schematic block diagram of part of the illustrative atherectomy system of FIG. 1, intended for multiple uses.

FIG. 2 is a schematic block diagram of the multiple use assembly 12. The multiple use assembly 12 includes a drive motor 16 that includes an output shaft 18. The output shaft 18 may be operably coupled to a rotor (not shown) within the drive motor 16, such that the output shaft 18 rotates in response to the rotor rotating within the drive motor 16. In some cases, the drive motor 16 is an electric drive motor, but this is not required in all cases. A first magnetic coupling segment 20 is rotatably coupled to the output shaft 18. As a result, the first magnetic coupling segment 20 can rotate when the output shaft 18 rotates. It will be appreciated that by including a second magnetic coupling segment (to be discussed) as part of the single use assembly 14, the drive shaft of the single use assembly 14 can be operably coupled with the drive motor 16. Using a magnetic coupling that includes the first magnetic coupling segment 20 and the second magnetic coupling segment provides an easy way to provide a repeatable connection between the drive motor 16 and ultimately an atherectomy burr. Using a magnetic coupling also enables a "clean" connection between the multiple use assembly 12 and each of the single use assemblies 14 used with the multiple use assembly 12 as any possible contaminants are kept well away from the multiple use assembly 12.

The multiple use assembly 12 includes a controller 22 that is adapted to control operation of the drive motor 16. In some cases, the controller 22 may be a PID controller that utilizes a Proportional (P) gain, an Integral (I) gain and a Derivative (D) gain as well as one or more feedback and/or reference signals in generating an output signal to the drive motor 16. In some instances, the multiple use assembly 12 may include a user interface 24 that is operably coupled with the controller 22. The user interface 24 may be used to input settings and other information, for example. In some cases, the user interface 24 may include a display that is adapted to display information provided by the controller 22.

In some cases, the multiple use assembly 12 may be considered as including a multiple use assembly housing 26. The first magnetic coupling segment 20 may extend through a side wall of the multiple use assembly housing 26 so that it is easy to see where to couple the single use assembly 14. In some instances, if the multiple use assembly housing 26 is polymeric, the first magnetic coupling segment 20 may remain just inside of the multiple use assembly housing 26. In such cases, the multiple use assembly housing 26 may include a marking indicating where the single use assembly 14 should be located in order to magnetically couple with the first magnetic coupling segment 20. It will be appreciated that the drive motor 16 and the controller 22 are both disposed within the multiple use assembly housing 26.

Figure 3:
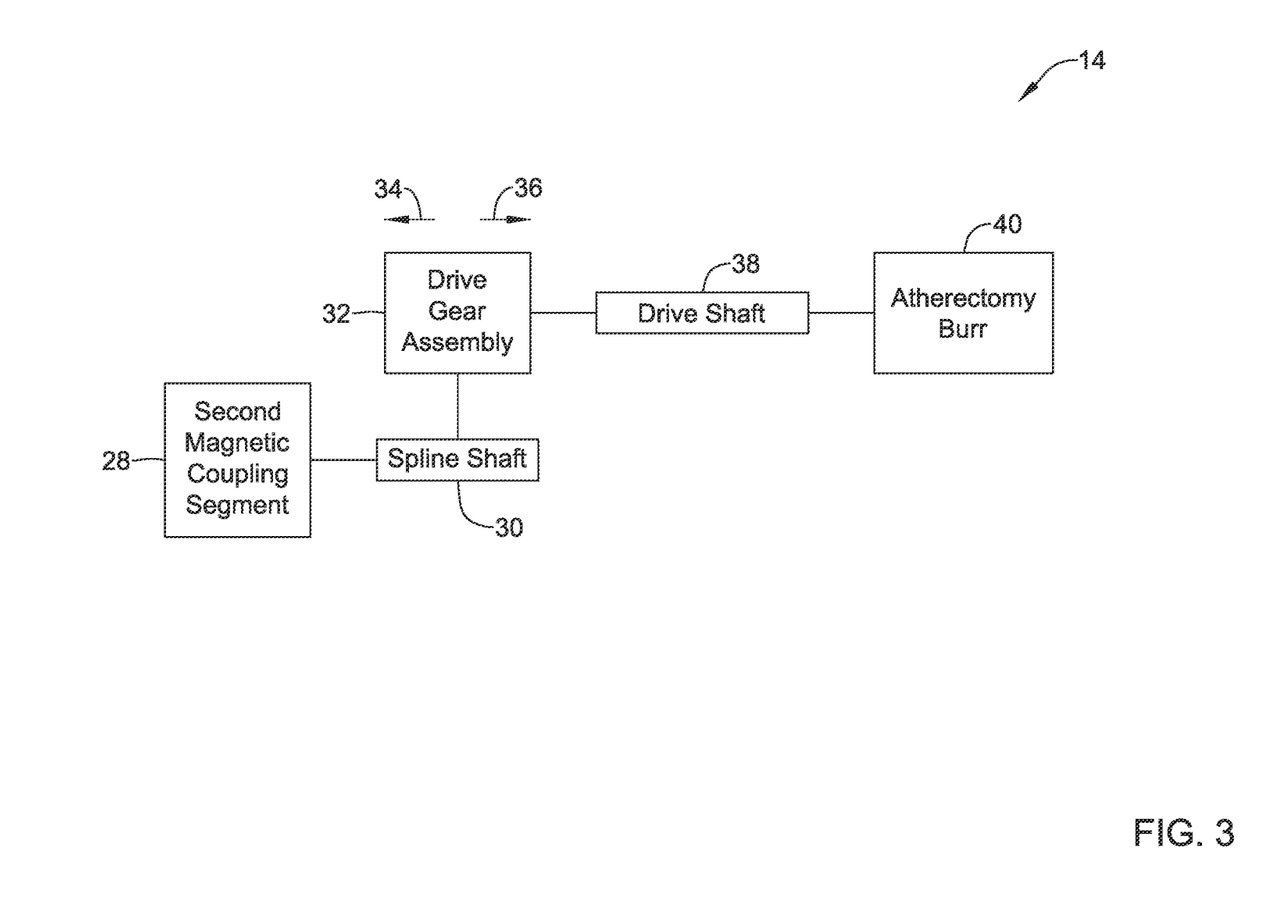
FIG. 3 is a schematic block diagram of part of the illustrative atherectomy system of FIG. 1, intended for single use.

FIG. 3 is a schematic block diagram of the single use assembly 14. The single use assembly 14 is releasably engageable with the multiple use assembly 12. The single use assembly 14 includes a second magnetic coupling segment 28 that is adapted to rotatably engage the first magnetic coupling segment 20 such that the second magnetic coupling element 28 rotates as the first magnetic coupling segment 20 rotates. It will be appreciated that the first magnetic coupling segment 20 and the second magnetic coupling segment 28 should have relative magnetic polarities that cause the first magnetic coupling segment 20 to be magnetically drawn towards the second magnetic coupling segment 28, and for the second magnetic coupling segment 28 to be magnetically drawn towards the first magnetic coupling segment 20, rather than the first magnetic coupling element 20 and the second magnetic coupling element 28 repelling each other. A North magnetic pole will attract a South magnetic pole and will repel a North magnetic pole. Similarly, a South magnetic pole will attract a North magnetic pole and will repel a South magnetic pole.

A spline shaft 30 is operably coupled with the second magnetic coupling segment 28 such that the spline shaft 30 rotates when the second magnetic coupling segment 28 rotates. A drive gear assembly 32 is translatable along the spline shaft 30, as indicated by arrows 34 and 36. The drive gear assembly 32 may be adapted to rotate in response to rotation of the spline shaft 30. As the drive gear assembly 32 rotates, a drive shaft 38 that is operably coupled with the drive gear assembly 32 is driven into rotation. The drive shaft 38 may be considered as being adapted to rotatably engage an atherectomy burr 40. In some cases, the drive shaft 38 may be adapted to rotatably engage any of a variety of different atherectomy burrs. For example, each of the variety of different atherectomy burrs may have a different diameter, for use in a variety of different sized blood vessels. In some cases, some of the atherectomy burrs 40 may vary in what is used as an abrasive material on a surface of the atherectomy burrs 40. In some instances, an atherectomy burr 40 may include one or more cutting elements formed in a surface of the atherectomy burr 40.

Figure 4:
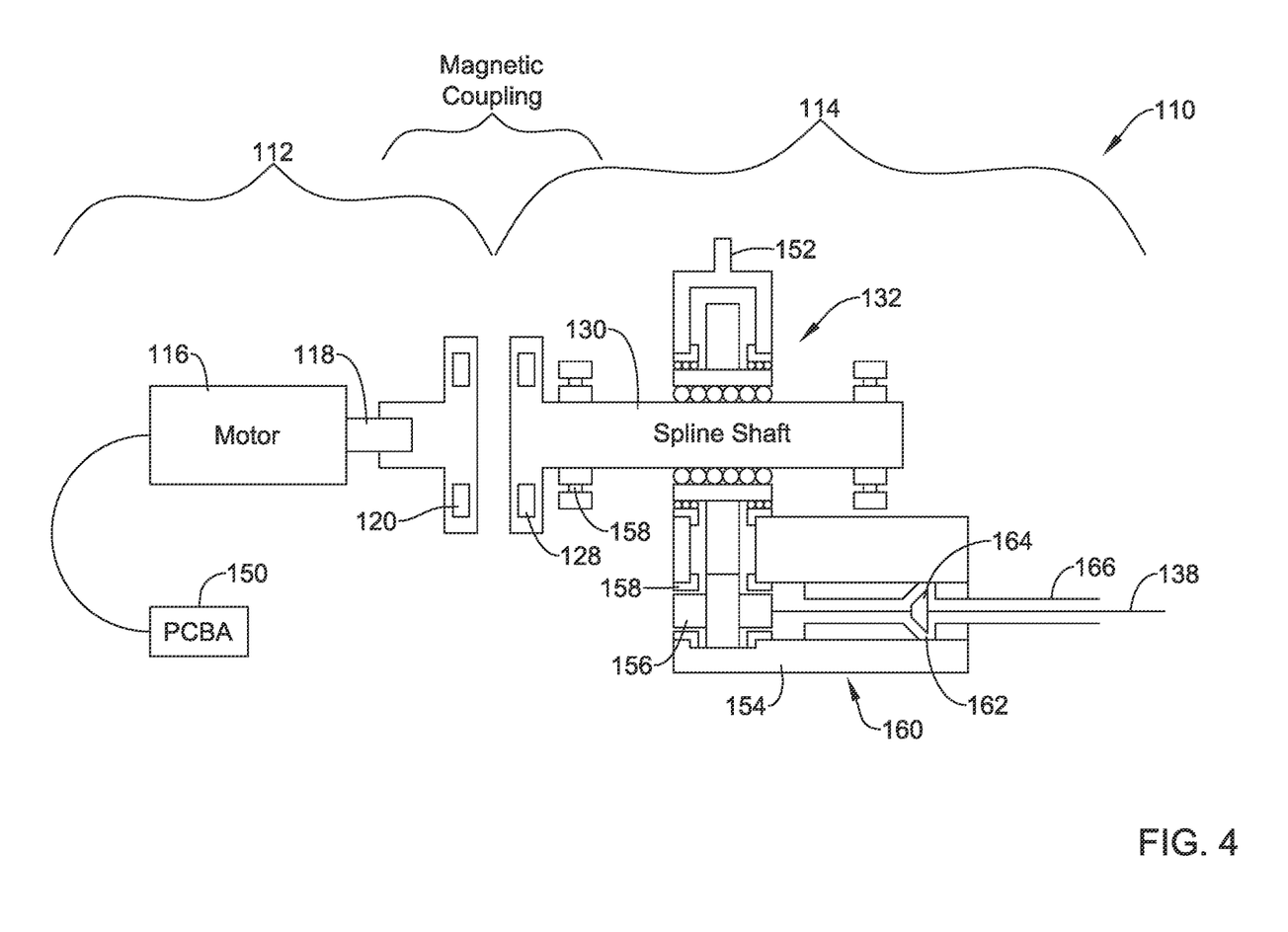
FIG. 4 is a schematic illustration of an illustrative atherectomy system.

FIG. 4 is a schematic illustration of an illustrative atherectomy system 110. The illustrative atherectomy system 110 may be considered as being an example of the illustrative atherectomy system 10. Features described as part of the atherectomy system 10 may be considered as being applicable to the atherectomy system 110, and features attributed to the atherectomy system 110 may be considered as being applicable to the atherectomy system 10. The atherectomy system 110 may be considered as including a multiple use assembly 112 and a single use assembly 114. As illustrated, the multiple use assembly 112 includes a drive motor 116 having an output shaft 118. A first magnetic coupling segment 120 is secured to the output shaft 118. The multiple use assembly 112 includes a Printed Circuit Board Assembly (PCBA) 150. It will be appreciated that the PCBA 150 may provide the functionality of the controller 22, for example.

The single use assembly 114 includes a second magnetic coupling segment 128 that magnetically engages the first magnetic coupling segment 120 such that the second magnetic coupling segment 128 rotates when the first magnetic coupling segment 120 rotates. A spline shaft 130 is coupled to the second magnetic coupling segment 128. A drive gear assembly 132 is adapted to translate along the spline shaft 130. As shown, the single use assembly 114 includes a translation handle 152 that can be grasped by an operator in order to translate the drive gear assembly 130 back and forth relative to the spline shaft 130, thereby moving a drive shaft 138 back and forth, thereby causing an atherectomy burr to translate back and forth without having to move the entirety of the atherectomy system 110.

The drive gear assembly 132 extends into a gear housing 154, where the drive gear assembly 132 engages a driven gear 156. Rotation of the drive gear assembly 132 causes rotation of the driven gear 156, which itself is coupled with and thus causes rotation of the drive shaft 138. It will be appreciated that each of the geared elements, including the spline shaft 130, components of the drive gear assembly 132 and the driven gear 156 are all supported by appropriate bearings 158. It will be appreciated that by changing relative gear diameters and other gear parameters, it is possible to provide a speed increase, a speed decrease or no change in speed to the drive shaft 138.

The gear housing 154 defines a pumping section 160. The pumping section 160 defines a pumping chamber 162 in which a rotor 164 is able to rotate as a result of being secured to the drive shaft 138. While not illustrated, it will be appreciated that there may be a saline source fluidly coupled with the gear housing 154 and hence with the pumping chamber 162. Rotation of the rotor 164 within the confines of the pumping chamber 162 causes fluid (saline) to be pumped through an interior of a hollow shaft 166 surrounding the drive shaft 138. The fluid pumped through the hollow shaft 166 serves to reduce heat that may be caused by rotation of the drive shaft 138 within the hollow shaft 166 and to reduce heat caused by rotation of the atherectomy burr as the atherectomy burr rotates against a vessel blockage. The fluid pumped through the hollow shaft 166 also serves to flush debris away from the atherectomy burr as the atherectomy burr rotates.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:
   a multiple use assembly including:
   a drive motor having an output shaft;
   a first magnetic coupling segment operably rotatably coupled to the output shaft; and
   a controller adapted to control operation of the drive motor; and
   a single use assembly releasably engageable with the multiple use assembly, the single use assembly including:
   a second magnetic coupling segment adapted to rotatably engage the first magnetic coupling segment;
   a spline shaft rotatably coupled with the second magnetic coupling segment;
   a drive gear assembly translatable along the spline shaft; and
   a drive shaft operably coupled with the drive gear assembly, the drive shaft adapted to rotatably engage an atherectomy burr;
   a gear housing adapted to translate relative to the spline shaft;
   a pumping section disposed within the gear housing; and
   a pump rotor operably secured to the drive shaft and disposed within the pumping section.

2. The atherectomy system of claim 1, wherein the multiple use assembly further comprises a user interface operably coupled with the controller.

3. The atherectomy system of claim 1, wherein the multiple use assembly includes one or more printed circuit boards that include the controller.

4. The atherectomy system of claim 1, wherein the multiple use assembly further comprises a multiple use assembly housing.

5. The atherectomy system of claim 4, wherein the drive motor is disposed within the multiple use assembly housing.

6. The atherectomy system of claim 4, wherein the controller adapted to control operation of the drive motor is disposed within the multiple use assembly housing.

7. The atherectomy system of claim 1, wherein the single use assembly further comprises a translation handle coupled to the gear housing, such that translating the translation handle causes the gear housing to translate relative to the spline shaft.

8. An atherectomy system, comprising:
   a housing;
   a drive motor disposed within the housing and including an output shaft extending to an exterior of the housing;
   a controller disposed within the housing and adapted to control operation of the drive motor;
   a first magnetic coupling segment rotatably coupled to the output shaft exterior to the housing; and
   a single use assembly comprising:
   a second magnetic coupling segment adapted to rotatably engage the first magnetic coupling segment;
   a spline shaft rotatably coupled with the second magnetic coupling segment;
   a drive gear assembly translatable along the spline shaft;
   a drive shaft operably coupled with the drive gear assembly, the drive shaft adapted to rotatably engage an atherectomy burr;
   a gear housing adapted to translate relative to the spline shaft; and
   a pumping section disposed within the gear housing.

9. The atherectomy system of claim 8, further comprising a pump rotor operably secured to the drive shaft and disposed within the pumping section.

10. The atherectomy system of claim 8, wherein the single use assembly further comprises a translation handle coupled to the gear housing, such that translating the translation handle causes the gear housing to translate relative to the spline shaft.

* * * * *